United States Patent
Lichenstein et al.

(10) Patent No.: US 10,751,345 B2
(45) Date of Patent: Aug. 25, 2020

(54) COMBINATION THERAPY WITH APILIMOD AND GLUTAMATERGIC AGENTS

(71) Applicant: AI Therapeutics, Inc., Guilford, CT (US)

(72) Inventors: Henri Lichenstein, Guilford, CT (US); Sean Landrette, Meriden, CT (US); Peter R. Young, Guilford, CT (US); Jonathan M. Rothberg, Guilford, CT (US)

(73) Assignee: AI Therapeutics, Inc., Guilford, CT (US)

( * ) Notice: Subject to any disclaimer, the term of this patent is extended or adjusted under 35 U.S.C. 154(b) by 0 days.

(21) Appl. No.: 16/280,106

(22) Filed: Feb. 20, 2019

(65) Prior Publication Data

US 2019/0255061 A1    Aug. 22, 2019

Related U.S. Application Data

(60) Provisional application No. 62/633,335, filed on Feb. 21, 2018.

(51) Int. Cl.
| | |
|---|---|
| *A61K 31/5375* | (2006.01) |
| *A61K 31/675* | (2006.01) |
| *A61K 31/66* | (2006.01) |
| *A61K 31/498* | (2006.01) |
| *A61K 31/5377* | (2006.01) |
| *A61P 25/00* | (2006.01) |
| *A61K 9/00* | (2006.01) |
| *A61K 31/428* | (2006.01) |
| *A61P 25/28* | (2006.01) |
| *A61K 45/06* | (2006.01) |
| *A61P 25/08* | (2006.01) |

(52) U.S. Cl.
CPC ........ *A61K 31/5377* (2013.01); *A61K 9/0053* (2013.01); *A61K 31/428* (2013.01); *A61K 45/06* (2013.01); *A61P 25/00* (2018.01); *A61P 25/08* (2018.01); *A61P 25/28* (2018.01)

(58) Field of Classification Search
CPC .. A61K 31/5375; A61K 31/675; A61K 31/66; A61K 31/498
USPC ........................ 514/231.2, 85, 114, 249, 250
See application file for complete search history.

(56) References Cited

U.S. PATENT DOCUMENTS

| | | | |
|---|---|---|---|
| 7,863,270 | B2 | 1/2011 | Demko et al. |
| 7,923,557 | B2 | 4/2011 | Zhang et al. |
| 2009/0118291 | A1 | 5/2009 | Belevedere et al. |
| 2011/0081338 | A1 | 4/2011 | Roberts et al. |
| 2011/0287018 | A1 | 11/2011 | Bosch |
| 2013/0267521 | A1 | 10/2013 | Castro et al. |
| 2016/0003804 | A1 | 1/2016 | Lu et al. |
| 2017/0007613 | A1 | 1/2017 | Lichenstein et al. |
| 2018/0015098 | A1 | 1/2018 | Lichenstein et al. |
| 2018/0217130 | A1 | 8/2018 | Lu et al. |

FOREIGN PATENT DOCUMENTS

| | | |
|---|---|---|
| WO | WO-2005/046619 | 5/2005 |
| WO | WO-2006/128129 A2 | 11/2006 |
| WO | WO-2006/128129 A3 | 11/2006 |
| WO | WO-2008/008433 A2 | 1/2008 |
| WO | WO-2008/008433 A3 | 1/2008 |
| WO | WO-2015/112888 | 7/2015 |
| WO | 2016081466 A1 | 5/2016 |
| WO | WO-2016/126707 A1 | 8/2016 |
| WO | 2016210372 A2 | 12/2016 |
| WO | 2017015262 A1 | 1/2017 |
| WO | 2017201501 A1 | 11/2017 |
| WO | WO-2018/071548 | 4/2018 |
| WO | 2019/164861 A1 | 8/2019 |

OTHER PUBLICATIONS

Cai, X. et al. (Jul. 25, 2013). PIKfyve, a class III PI kinase, is the target of the small molecular IL-12/IL-23 inhibitor apilimod and a player in Toll-like receptor signaling, *Chemistry and Biology* 20(7):912-921.
International Search Report dated Apr. 14, 2016 for International Application No. PCT/US2016/016177, filed Feb. 2, 2016.
Krausz, S et al., "A Phase IIa, Randomized, Double-Blind, Placebo-Controlled Trial of Apilimod Mesylate, an Interleukin-12/Interleukin-23 Inhibitor, in Patients with Rheumatoid Arthritis," *Arthritis & Rheumatism*, Jun. 2012, vol. 64, No. 6, pp. 1750-1755.
Lenk, G.M. et al., "Pathogenic Mechanism of the FIG4 Mutation Responsible for Charcot-Marie-Tooth Disease CMT4J", *PLOS Genetics*, Jun. 2011, vol. 7, No. 6, pp. 1-13.
Vaccari, I. et al., "Genetic Interaction Between MTMR2 and FIG4 Phospholipid Phosphates Involved in Charcot-Marie-Tooth Neuropathies," *PLOS Genetics*, Oct. 2011, vol. 7, No. 10, pp. 1-15.
Bhakar et al. (Oct. 1, 2002) "Constitutive nuclear factor -kB activity is required for central neuron survival". The Journal of Neuroscience 22(19):8466-8475.
Singh et al. (1997) "Circulating cytokines in Alzheimer's disease", J. Psychiat. Res., vol. 31 No. 6 pp. 657-660.
Delague "Charcot-Marie-Tooth Neuropathy Type 4H," *GeneReviews*, 2013, Editors: Adam MP, et al. https://www.ncbi.nlnn.nih.gov/books/NBK153601/?report=printable.
Shi, Y. et al. (Feb. 5, 2018). "Haploinsufficiency leads to neurodegeneration in C9ORF72 ALS/FTD human induced motor neurons." Nature Medicine 24(3):313-325.
Alzforum, M. et al. (Feb. 9, 2018). "Lack of C9ORF72 protein renders neurons more vulnerable to degeneration." ALS Research Forum. Whole document retrieved from the Internet on May 24, 2019: URL:http://www.alsresearchforum.org/lack-of-c9orf72-protein-renders-neurons-more-vulnerable-to-degeneration/. 6 pages.

(Continued)

*Primary Examiner* — Raymond J Henley, III
(74) *Attorney, Agent, or Firm* — Mintz Levin Cohn Ferris Glovsky and Popeo, P.C.; Muriel Liberto, Esq.

(57) ABSTRACT

Provided are compositions and methods related to the use of apilimod in combination with glutamatergic agents for treating neurological diseases and disorders, and for the treatment of cancer.

30 Claims, 1 Drawing Sheet

(56) References Cited

OTHER PUBLICATIONS

International Search Report and Written Opinion dated Jun. 18, 2019 for International Patent Application No. PCT/US2019/018662, filed on Feb. 20, 2019. 14 pages.

Nagahara et al. (Sep. 25, 2013) "Early BDNF Treatment Ameliorates Cell Loss in the Entorhinal Cortex of APP Transgenic Mice." The Journal of Neuroscience, 33(39):15596-15602.

Ritchie et al. (Jan. 20, 2015) "Limma Powers Differential Expression Analyses for RNA-Sequencing and Microarray Studies." Nucleic Acids Research, 43(7):13 pages.

Wada et al. (Oct. 19, 2006) "Selective Abrogation of Th1 Response by STA-5326, a Potent IL-12/IL-23 Inhibitor." Blood, 109(3):1156-1164.

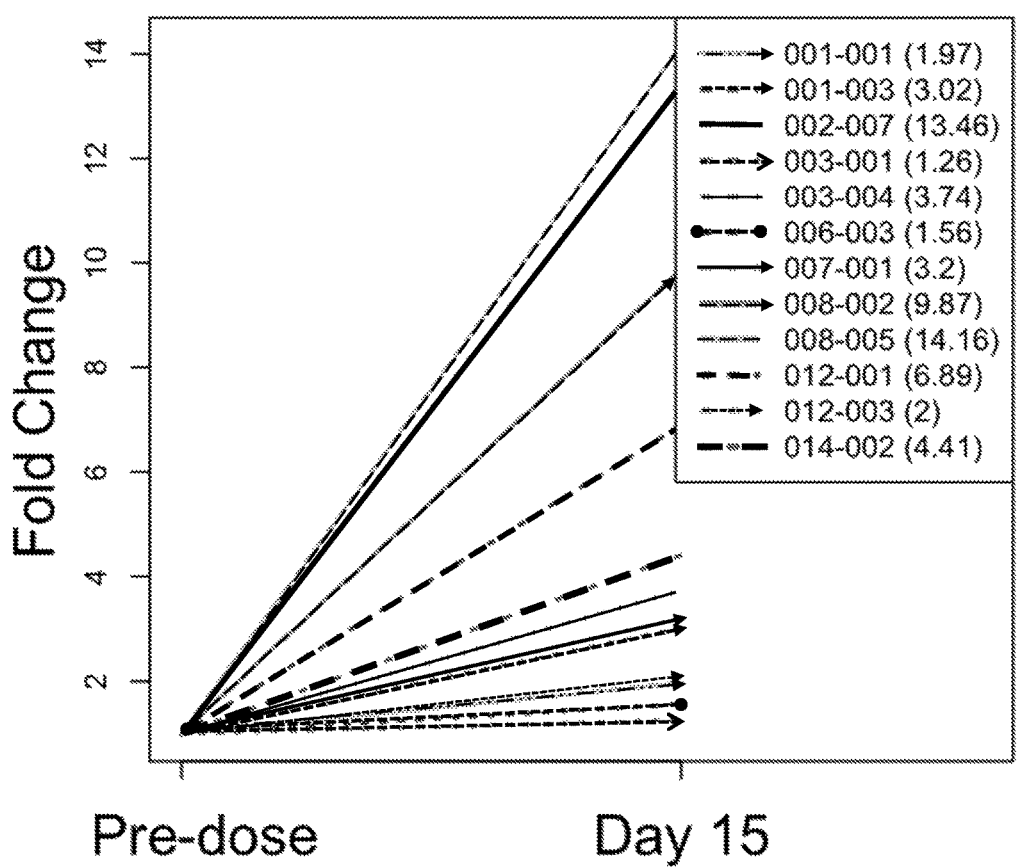

COMBINATION THERAPY WITH APILIMOD AND GLUTAMATERGIC AGENTS

CROSS-REFERENCE TO RELATED APPLICATIONS

This application claims the benefit of priority from U.S. Provisional Application Ser. No. 62/633,335, filed on Feb. 21, 2018, the contents of which are hereby incorporated herein by reference in their entirety.

FIELD OF THE DISCLOSURE

The present disclosure relates to compositions and methods comprising apilimod for use in combination with glutamatergic agents in the treatment of neurological diseases and disorders, and cancer.

BACKGROUND OF THE DISCLOSURE

Apilimod, also referred to as STA-5326, hereinafter "apilimod", is recognized as a potent transcriptional inhibitor of IL-12 and IL-23. See e.g., Wada et al. *Blood* 109 (2007): 1156-1164. IL-12 and IL-23 are inflammatory cytokines normally produced by immune cells, such as B-cells and macrophages, in response to antigenic stimulation. Autoimmune disorders and other disorders characterized by chronic inflammation are characterized in part by inappropriate production of these cytokines. In immune cells, the selective inhibition of IL-12/IL-23 transcription by apilimod was recently shown to be mediated by apilimod's direct binding to phosphatidylinositol-3-phosphate 5-kinase (PIKfyve). See, e.g., Cai et al. *Chemistry and Biol.* 20 (2013):912-921. PIKfyve plays a role in Toll-like receptor signaling, which is important in innate immunity.

Some neurodegenerative diseases result in the accumulation of protein aggregates or other intermediates of cellular catabolism that may lead to neural toxicity and degeneration.

Glutamate, also referred to as glutamic acid, is the main excitatory neurotransmitter in humans. It is also a substrate in the synthesis of the main inhibitory neurotransmitter, GABA (γ-Aminobutyric acid), which regulates neuronal excitability.

Glutamate transporters are a family of neurotransmitter transporter proteins that move glutamate across neural cell membranes. Glutamate transporters include two main classes, the excitatory amino acid transporters and the vesicular glutamate transporters. The amino acid transporters remove glutamate from the synaptic cleft by stimulating reuptake into neural cells. The vesicular transporters move glutamate intracellularly from the cell cytoplasm into synaptic vesicles.

Glutamate excitotoxicity refers to a pathological process by which neural cells are damaged or destroyed by excessive glutamate stimulation. High levels of glutamate cause the over-stimulation of glutamate receptors such as the N-methyl-D-aspartate (NMDA) and AMPA receptors, setting in motion the pathological activation of various intracellular enzymes that results in damage to cellular structures including the cytoskeleton, membranes, and even DNA.

Glutamate excitotoxicity is implicated in various neurological diseases and disorders including spinal cord injury, stroke, and traumatic brain injury, as well as in certain neurodegenerative diseases of the central nervous system including multiple sclerosis, Alzheimer's disease, amyotrophic lateral sclerosis (ALS), Parkinson's disease, alcoholism or alcohol withdrawal and Huntington's disease.

SUMMARY OF THE DISCLOSURE

The present disclosure provides methods for treating a neurological disease or disorder and methods for treating cancer in a subject in need thereof, the method comprising administering to the subject a pharmaceutical composition comprising apilimod, or a pharmaceutically acceptable salt thereof, in combination with a glutamatergic agent.

In embodiments, the disclosure provides a method for treating a neurological disease or disorder in a subject in need thereof, the method comprising administering to the subject a pharmaceutical composition comprising apilimod, or a pharmaceutically acceptable salt thereof, in combination with a glutamatergic agent. In embodiments, the apilimod is apilimod dimesylate. In embodiments, the glutamatergic agent is selected from a glutamate transporter modulating agent and a glutamate receptor antagonist. In embodiments, the glutamate transporter modulating agent is an excitatory amino acid reuptake inhibitor. In embodiments, the glutamate receptor antagonist is an N-methyl-D-aspartate (NMDA) receptor antagonist. In embodiments, the glutamate receptor antagonist is selected from AP5 (R-2-amino-5-phosphonopentanoate), AP7 (2-amino-7-phosphonoheptanoic acid), CNQX (6-cyano-7-nitroquinoxaline-2,3-dione), CPPene (3-[(R)-2-carboxypiperazin-4-yl]-prop-2-enyl-1-phosphonic acid), NBQX (2,3-dihydroxy-6-nitro-7-sulfamoyl-benzo[f]quinoxaline-2,3-dione), and selfotel (CGS-19755). In embodiments, the glutamate receptor antagonist is selected from amantadine, atomoxetine, AZD6765, agmatine, gacyclidine, ketamine, memantine, eliprodil, delucemin. In embodiments, the glutamatergic agent is selected from BHV-5000, lamotrigine, lanicemine, riluzole, trigriluzole, and topiramate. In embodiments, the pharmaceutical composition is an oral dosage form or a sublingual dosage form. In embodiments, the glutamatergic agent is administered in the same or a different dosage form as the apilimod.

In embodiments, the neurological disease or disorder is selected from Alzheimer's disease, amyotrophic lateral sclerosis (ALS), attention deficit hyperactivity disorder, autism, cerebellar ataxia, Charcot-Marie-Tooth disease, Creutzfeldt-Jakob disease, dementia, epilepsy, Friedreich's ataxia, Huntington's disease, multiple sclerosis, obsessive compulsive disorder (OCD), Parkinson's disease, Rett syndrome, senile chorea, spinal ataxia, spinal cord injury, supranuclear palsy, traumatic brain injury.

In embodiments, the neurological disease or disorder is dementia. In embodiments, the dementia is selected from AIDS dementia complex (ADC), dementia associated with Alzheimer's disease (AD), dementia pugilistica, diffuse Lewy body disease, frontotemporal dementia, mixed dementia, senile dementia of Lewy body type, and vascular dementia.

In certain embodiments for the treatment of frontotemporal dementia or ALS, the patient in need of treatment of is one having repeat expansions in the C9ORF72 gene.

In embodiments, the neurological disease or disorder is amyotrophic lateral sclerosis (ALS).

In embodiments, the neurological disease or disorder is Rett syndrome.

In embodiments, the neurological disease or disorder is obsessive compulsive disorder (OCD).

In embodiments, the subject is human.

The disclosure also provides a method for treating amyotrophic lateral sclerosis (ALS) in a subject in need thereof, the method comprising administering to the subject a pharmaceutical composition comprising apilimod, or a pharmaceutically acceptable salt thereof, in combination with a glutamatergic agent selected from riluzole and trigriluzole.

The disclosure also provides a method for treating Alzheimer's disease in a subject in need thereof, the method comprising administering to the subject a pharmaceutical composition comprising apilimod, or a pharmaceutically acceptable salt thereof, in combination with a glutamatergic agent selected from riluzole and trigriluzole.

The disclosure also provides a method for treating obsessive compulsive disorder (OCD) in a subject in need thereof, the method comprising administering to the subject a pharmaceutical composition comprising apilimod, or a pharmaceutically acceptable salt thereof, in combination with a glutamatergic agent selected from riluzole and trigriluzole.

The disclosure also provides a method for treating Rett syndrome in a subject in need thereof, the method comprising administering to the subject a pharmaceutical composition comprising apilimod, or a pharmaceutically acceptable salt thereof, in combination with a glutamatergic agent selected from BHV-5000, and lanicemine.

The disclosure also provides a method of treating cancer in a subject in need thereof, the methods comprising administering to the subject a pharmaceutical composition comprising apilimod, or a pharmaceutically acceptable salt thereof, in combination with a glutamatergic agent selected from riluzole and trigriluzole, preferably trigriluzole. In embodiments, the cancer is selected from brain cancer, breast cancer, cervical cancer, colorectal cancer, leukemia, lung cancer, lymphoma, melanoma or other skin cancer, ovarian cancer, prostate cancer, renal cancer, and testicular cancer.

The disclosure also provides a pharmaceutical composition comprising apilimod for use in combination therapy with a glutamatergic agent in the treatment of a neurological disease or disorder, or for the treatment of cancer. In embodiments, the apilimod is apilimod dimesylate. In embodiments, the glutamatergic agent is selected from a glutamate transporter modulating agent and a glutamate receptor antagonist. In embodiments, the glutamate transporter modulating agent is an excitatory amino acid reuptake inhibitor. In embodiments, the glutamate receptor antagonist is an N-methyl-D-aspartate (NMDA) receptor antagonist. In embodiments, the glutamate receptor antagonist is selected from amantadine, atomoxetine, AZD6765, agmatine, gacyclidine, memantine, eliprodil, delucemin. In embodiments, the glutamatergic agent is selected from riluzole, trigriluzole, BHV-5000, and lanicemine. In embodiments, the apilimod and the glutamatergic agent are contained in the same dosage form.

In embodiments, the pharmaceutical composition is for use in treating a neurological disease or disorder selected from Alzheimer's disease, amyotrophic lateral sclerosis (ALS), attention deficit hyperactivity disorder, autism, cerebellar ataxia, Charcot-Marie-Tooth disease, Creutzfeldt-Jakob disease, dementia, epilepsy, Friedreich's ataxia, Huntington's disease, multiple sclerosis, obsessive compulsive disorder (OCD), Parkinson's disease, Rett syndrome, senile chorea, spinal ataxia, spinal cord injury, supranuclear palsy, and traumatic brain injury. In embodiments, the neurological disease or disorder is dementia. In embodiments, the dementia is selected from AIDS dementia complex (ADC), dementia associated with Alzheimer's disease (AD), dementia pugilistica, diffuse Lewy body disease, frontotemporal dementia, mixed dementia, senile dementia of Lewy body type, and vascular dementia. In embodiments, the neurological disease or disorder is amyotrophic lateral sclerosis (ALS). In embodiments, the neurological disease or disorder is Rett syndrome. In embodiments, the neurological disease or disorder is obsessive compulsive disorder (OCD)

BRIEF DESCRIPTION OF THE FIGURES

FIG. 1: Fold change of plasma (shed) GPNMB after 14 days of dosing between pre-dose and day 15 in 12 patients. The fold change for each patient is indicated parentheses in the key in the upper right corner of the graph.

DETAILED DESCRIPTION OF THE DISCLOSURE

The present disclosure provides compositions and methods related to the use of apilimod for treating neurological diseases and disorders, and cancer, particularly in combination with modulators of the glutamate transporter/receptor system. Accordingly, the disclosure provides methods for treating a neurological disease or disorder and methods for treating cancer in a subject in need thereof, comprising administering apilimod, or a pharmaceutically acceptable salt thereof, in combination with a glutamatergic agent.

The term "apilimod" refers to 2-[2-Pyridin-2-yl)-ethoxy]-4-N'-(3-methyl-benzilidene)-hydrazino]-6-(morpholin-4-yl)-pyrimidine (IUPAC name: (E)-4-(6-(2-(3-methylbenzylidene)hydrazinyl)-2-(2-(pyridin-2-yl)ethoxy)pyrimidin-4-yl)morpholine), represented by Formula I:

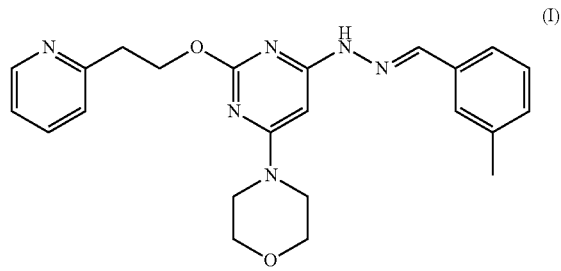 [SMILES: Cc1cccc(/C=N/Nc2cc(N3CCOCC3)nc(OCCc3ccccn3)n2)c1]

The CAS number of apilimod is 541550-19-0.

Apilimod can be prepared, for example, according to the methods described in U.S. Pat. Nos. 7,923,557, and 7,863,270, and WO 2006/128129.

In embodiments of the compositions and methods described here, a pharmaceutically acceptable salt, solvate, clathrate, hydrate, polymorph, metabolite, prodrug, analog or derivative of apilimod may be used in the compositions and methods for treating a neurological disease or disorder.

The term "pharmaceutically acceptable salt," is a salt formed from, for example, an acid and a basic group of a compound described herein (e.g., 2-[2-Pyridin-2-yl)-ethoxy]-4-N'-(3-methyl-benzilidene)-hydrazino]-6-(morpholin-4-yl)-pyrimidine). Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (e.g., 1,1'-methylene-bis-(2-hydroxy-3-naphthoate)) salts. In a preferred embodiment, the salt of apilimod comprises methanesulfonate. The term "pharmaceutically acceptable salt" also refers to a salt prepared from a compound described herein (e.g., 2-[2-Pyridin-2-yl)-ethoxy]-4-N'-(3-methyl-benzilidene)-hydrazino]-6-(morpholin-4-yl)-pyrimidine), having an acidic functional group, such as a carboxylic acid functional group, and a pharmaceutically acceptable inorganic or organic base.

Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound described herein (e.g., 2-[2-Pyridin-2-yl)-ethoxy]-4-N'-(3-methyl-benzilidene)-hydrazino]-6-(morpholin-4-yl)-pyrimidine), having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

The salts of the compounds described herein (e.g., 2-[2-Pyridin-2-yl)-ethoxy]-4-N'-(3-methyl-benzilidene)-hydrazino]-6-(morpholin-4-yl)-pyrimidine) can be synthesized from the parent compound (e.g., 2-[2-Pyridin-2-yl)-ethoxy]-4-N'-(3-methyl-benzilidene)-hydrazino]-6-(morpholin-4-yl)-pyrimidine) by conventional chemical methods such as methods described in Pharmaceutical Salts: Properties, Selection, and Use, P. Hemrich Stalil (Editor), Camille G. Wermuth (Editor), ISBN: 3-90639-026-8, August 2002. Generally, such salts can be prepared by reacting the parent compound (e.g., 2-[2-Pyridin-2-yl)-ethoxy]-4-N'-(3-methyl-benzilidene)-hydrazino]-6-(morpholin-4-yl)-pyrimidine) with the appropriate acid in water or in an organic solvent, or in a mixture of the two.

One salt form of a compound described herein (e.g., 2-[2-Pyridin-2-yl)-ethoxy]-4-N'-(3-methyl-benzilidene)-hydrazino]-6-(morpholin-4-yl)-pyrimidine) can be converted to the free base and optionally to another salt form by methods well known to the skilled person. For example, the free base can be formed by passing the salt solution through a column containing an amine stationary phase (e.g. a Strata-$NH_2$ column). Alternatively, a solution of the salt in water can be treated with sodium bicarbonate to decompose the salt and precipitate out the free base. The free base may then be combined with another acid using routine methods.

The term "polymorph" means solid crystalline forms of a compound of the present disclosure (e.g., 2-[2-Pyridin-2-yl)-ethoxy]-4-N'-(3-methyl-benzilidene)-hydrazino]-6-(morpholin-4-yl)-pyrimidine) or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "hydrate" means a compound of the present disclosure (e.g., 2-[2-Pyridin-2-yl)-ethoxy]-4-N'-(3-methyl-benzilidene)-hydrazino]-6-(morpholin-4-yl)-pyrimidine) or a salt thereof, which further includes a stoichiometric or non-stoichiometric amount of water bound by non-covalent intermolecular forces.

The term "clathrate" means a compound of the present disclosure (e.g., 2-[2-Pyridin-2-yl)-ethoxy]-4-N'-(3-methyl-benzilidene)-hydrazino]-6-(morpholin-4-yl)-pyrimidine) or a salt thereof in the form of a crystal lattice that contains spaces (e.g., channels) that have a guest molecule (e.g., a solvent or water) trapped within.

The term "prodrug" means a derivative of a compound described herein (e.g., 2-[2-Pyridin-2-yl)-ethoxy]-4-N'-(3-methyl-benzilidene)-hydrazino]-6-(morpholin-4-yl)-pyrimidine) that can hydrolyze, oxidize, or otherwise react under biological conditions (in vitro or in vivo) to provide a compound of the disclosure. Prodrugs may only become active upon such reaction under biological conditions, or they may have activity in their unreacted forms. Examples of prodrugs contemplated in this disclosure include, but are not limited to, analogs or derivatives of a compound described herein (e.g., 2-[2-Pyridin-2-yl)-ethoxy]-4-N'-(3-methyl-benzilidene)-hydrazino]-6-(morpholin-4-yl)-pyrimidine) that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —$NO_2$, —ONO, or —$ONO_2$ moieties. Prodrugs can typically be prepared using well-known methods, such as those described by Burger's Medicinal Chemistry and Drug Discovery (1995) 172-178, 949-982 (Manfred E. Wolff ed., 5th ed).

In addition, some of the compounds suitable for use in the methods of in this disclosure (e.g., 2-[2-Pyridin-2-yl)-ethoxy]-4-N'-(3-methyl-benzilidene)-hydrazino]-6-(morpholin-4-yl)-pyrimidine) have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present disclosure. The compounds of this disclosure (e.g., 2-[2-Pyridin-2-yl)-ethoxy]-4-N'-(3-methyl-benzilidene)-hydrazino]-6-(morpholin-4-yl)-pyrimidine) can also be represented in multiple tautomeric forms, in such instances, the disclosure expressly includes all tautomeric forms of the compounds described herein (e.g., there may be a rapid equilibrium of multiple structural forms of a compound), the disclosure expressly includes all such reaction products). All such isomeric forms of such compounds are expressly included in the present disclosure. All crystal forms of the compounds described herein (e.g., 2-[2-Pyridin-2-yl)-ethoxy]-4-N'-(3-methyl-benzilidene)-hydrazino]-6-(morpholin-4-yl)-pyrimidine) are expressly included in the present disclosure.

The term "solvate" or "pharmaceutically acceptable solvate," is a solvate formed from the association of one or more solvent molecules to one of the compounds disclosed herein (e.g., 2-[2-Pyridin-2-yl)-ethoxy]-4-N'-(3-methyl-benzilidene)-hydrazino]-6-(morpholin-4-yl)-pyrimidine). The term solvate includes hydrates (e.g., hemi-hydrate, monohydrate, dihydrate, trihydrate, tetrahydrate, and the like).

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. As used herein, the term "derivative" refers to compounds that have a common core structure, and are substituted with various groups as described herein.

In certain embodiments of the disclosure described herein, apilimod, or a pharmaceutically acceptable salt, hydrate, clathrate, or prodrug of apilimod, as described above, may be provided in combination with one or more additional therapeutic agents. In accordance with any of these embodiments, the apilimod, or a pharmaceutically acceptable salt, solvate, clathrate, hydrate, polymorph, metabolite, prodrug, analog or derivative thereof, may be provided in the same dosage form as the one or more additional therapeutic agents, or in a separate dosage form.

Methods of Treatment

The present disclosure provides methods for treating a neurological disease or disorder, or a cancer, in a subject in need thereof comprising administering apilimod, or a pharmaceutically acceptable salt, solvate, clathrate, hydrate, polymorph, metabolite, prodrug, analog or derivative thereof, in combination with a glutamatergic agent. The present disclosure further provides the use of apilimod, or a pharmaceutically acceptable salt, solvate, clathrate, hydrate, polymorph, metabolite, prodrug, analog or derivative thereof, in combination with a glutamatergic agent for the preparation of a medicament useful for the treatment of a neurological disease or disorder, or a cancer.

In embodiments, the glutamatergic agent is selected from a glutamate transporter modulating agent and a glutamate receptor antagonist. In embodiments, the glutamate transporter modulating agent is an excitatory amino acid reuptake inhibitor. In embodiments, the glutamate receptor antagonist is an N-methyl-D-aspartate (NMDA) receptor antagonist. In embodiments, the glutamate receptor antagonist is an antagonist of the α-amino-3-hydroxy-5-methyl-4-isoxazole-propionic acid receptor (AMPA) receptor, or the kainite receptor.

In embodiments, the glutamatergic agent is a glutamate receptor antagonist selected from AP5 (R-2-amino-5-phosphonopentanoate), AP7 (2-amino-7-phosphonoheptanoic acid), CNQX (6-cyano-7-nitroquinoxaline-2,3-dione), CPPene (3-[(R)-2-carboxypiperazin-4-yl]-prop-2-enyl-1-phosphonic acid), NBQX (2,3-dihydroxy-6-nitro-7-sulfamoyl-benzo[f]quinoxaline-2,3-dione), and selfotel (CGS-19755).

In embodiments, the glutamatergic agent is a glutamate receptor antagonist selected from amantadine, atomoxetine, AZD6765, agmatine, gacyclidine, ketamine, memantine, eliprodil, delucemin.

In embodiments, the glutamatergic agent is selected from BHV-5000, lamotrigine, lanicemine, riluzole, trigriluzole, and topiramate.

The methods described here relate to combination therapy with apilimod and at least one glutamatergic agent. The terms, "combination therapy" or "co-therapy" include the administration of a compound described herein, e.g., apilimod, or a pharmaceutically acceptable salt, solvate, clathrate, hydrate, polymorph, metabolite, prodrug, analog or derivative thereof, with at least one additional agent, e.g., a glutamatergic agent, as part of a specific treatment regimen intended to provide a beneficial effect from the co-action of these compounds. The beneficial effect may result in the slowing of the progression of the neurological disease or disorder, or the cancer, and/or the alleviation of one or more symptoms of the neurological disease or disorder, or the cancer. The beneficial effect of the combination includes, but is not limited to, pharmacokinetic or pharmacodynamic co-action resulting from the combination. The beneficial effect of the combination may also relate to the mitigation of a toxicity, side effect, or adverse event associated with another agent in the combination. "Combination therapy" is not intended to encompass the administration of two or more of these therapeutic compounds as part of separate monotherapy regimens that incidentally and arbitrarily result in the combinations of the present disclosure.

In the context of combination therapy, administration of apilimod, or a pharmaceutically acceptable salt, solvate, clathrate, hydrate, polymorph, metabolite, prodrug, analog or derivative thereof, may be simultaneous with or sequential to the administration of the glutamatergic agent. In another aspect, administration of the different components of a combination therapy may be at different frequencies. The one or more additional agents may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a compound of the present disclosure.

The therapeutic agents can be formulated for co-administration in a single dosage form, or they can be administered separately in different dosage forms. When administered separately, administration may be by the same or a different route of administration for each of the components of the combination therapy.

Preferably, combination therapy provides a synergistic response. The term "synergistic" refers to the efficacy of the combination being more than the additive effects of either single therapy alone. The synergistic effect of combination therapy may permit the use of lower dosages and/or less frequent administration of at least one agent in the combination compared to its dose and/or frequency outside of the combination. The synergistic effect may also be manifested in the avoidance or reduction of adverse or unwanted side effects associated with the use of either therapy in the combination alone.

In embodiments of the methods described herein, apilimod, or a pharmaceutically acceptable salt, solvate, clathrate, hydrate, polymorph, metabolite, prodrug, analog or derivative thereof, may be administered at the same time or at a different time, the context of the combination therapy with the glutamatergic agent. In embodiments, the apilimod, or a pharmaceutically acceptable salt, solvate, clathrate, hydrate, polymorph, metabolite, prodrug, analog or derivative thereof, and the glutamatergic agent are administered in a single dosage form, or in separate dosage forms.

In embodiments, the combination therapy with apilimod and a glutamatergic agent further includes an additional agent that mitigates one or more side effects of apilimod, for example, nausea, vomiting, headache, dizziness, lightheadedness, drowsiness and stress. In one aspect of this embodiment, the additional agent is a serotonin receptor antagonist, also known as 5-hydroxytryptamine receptors or 5-HT receptors. In one aspect, the additional agent is an antagonist of a $5-HT_3$ or $5-HT_{1a}$ receptor. In one aspect, the agent is selected from the group consisting of ondansetron, granisetron, dolasetron and palonosetron. In another aspect, the agent is selected from the group consisting of pindolol and risperidone.

In accordance with the methods described here, the neurological disease or disorder may be selected from a neurodegenerative disease or disorder, epilepsy, a neuromuscular disorder, or a neurodevelopmental disorder.

Neurodegenerative diseases and disorders that may be treated according to the methods described here include, for example, Alzheimer's disease (AD), amyotrophic lateral sclerosis (ALS), diffuse Lewy body disease, motor neuron diseases, multiple sclerosis (MS), Parkinson's disease (PD), Friedreich's ataxia, prion disease, spinocerebellar ataxia (SCA), and spinal muscular atrophy (SMA). Other, less common neurodegenerative diseases and disorders that may be treated include, for example, Creutzfeldt-Jakob disease (CJD), progressive supranuclear palsy (PSP, Steele-Richardson-Olszewski syndrome), senile chorea, Huntington's Chorea, spinal ataxia including spinocerebellar ataxia (SCA), Friedreich's ataxia, Subacute sclerosing panencephalitis, frontotemporal lobar degeneration, and Hallerrorden-Spatz disease (Pantothenate kinase-associated neurodegeneration, PKAN). In an embodiment for the treatment of ALS or frontotemporal dementia, the patient in need of treatment of is one having repeat expansions in the C9ORF72 gene.

Various forms of dementia may also be considered neurodegenerative diseases. In general, the term 'dementia' describes a group of symptoms affecting memory, thinking and social abilities severely enough to interfere with daily functioning. Accordingly, the disclosure also provides methods of treating dementia, including AIDS dementia complex (ADC), dementia associated with Alzheimer's disease (AD), dementia pugilistica, diffuse Lewy body disease, frontotemporal dementia, mixed dementia, senile dementia of Lewy body type, and vascular dementia. In an embodiment for the treatment of frontotemporal dementia, the patient in need of treatment of is one having repeat expansions in the C9ORF72 gene.

Neuromuscular disorders that may be treated according to the methods described here include, for example, infantile spinal muscular atrophy (SMA1, Werdnig-Hoffmann disease), and juvenile spinal muscular atrophy (SMA3, Kugelberg-Welander disease).

Neurodevelopmental disorders that may be treated according to the methods described here include Rett syndrome.

In accordance with the methods described here, the neurological disease or disorder may also be selected from bipolar disorder, treatment resistant and major depression, general anxiety disorder, panic disorder, social anxiety, mood disorders, cognitive disorders, agitation, apathy, psychoses, post-traumatic stress disorders, irritability, disinhibition, learning disorders, memory loss, personality disorders, bipolar disorders, eating disorders, conduct disorder, pain disorders, delirium, drug addiction, tinnitus, mental retardation, cervical spondylotic myelopathy, spinal cord injury, hereditary cerebellar ataxia, Tourette syndrome, autism spectrum disorder, schizophrenia, fragile X syndrome, Parkinson's Disease and Huntington's disease.

In embodiments for the treatment of Alzheimer's disease, the combination therapy with apilimod and a glutamatergic agent may form part of a therapeutic regimen including administration of a cholinesterase inhibitor (e.g., Aricept™, Exelon™, Razadyne™). In an embodiment for the treatment of Alzheimer's disease, the glutamatergic agent is selected from memantine (Namenda™) and trigriluzole.

In embodiments for the treatment of amyotrophic lateral sclerosis (ALS), the combination therapy with apilimod and a glutamatergic agent may form part of a therapeutic regimen including administration of an antioxidant, such as edaravone (Radicava™, Radicut™). In an embodiment for the treatment of ALS, the glutamatergic agent is selected from riluzole and trigriluzole. In an embodiment for the treatment of ALS, the glutamatergic agent is trigriluzole. In an embodiment for the treatment of ALS, the patient in need of treatment of is one having repeat expansions in the C9ORF72 gene.

In embodiments for the treatment of obsessive compulsive disorder (OCD), the combination therapy with apilimod and a glutamatergic agent may form part of a therapeutic regimen including administration of a selective serotonin reuptake inhibitor (SSRI), clomipramine, or an atypical antipsychotic such as risperidone. In an embodiment for the treatment of ALS, the glutamatergic agent is selected from riluzole and trigriluzole.

In embodiments for the treatment of Rett syndrome, the combination therapy with apilimod and a glutamatergic agent may form part of a therapeutic regimen including administration of a selective serotonin reuptake inhibitor (SSRI). In an embodiment for the treatment of Rett syndrome, the glutamatergic agent is selected from BHV-5000 and lanicemine.

In embodiments, the disclosure provides a method of treating a neurological disease or disorder selected from stroke, Alzheimer's disease, Parkinson's disease, schizophrenia, epilepsy and chronic pain in a subject in need thereof, the method comprising administering to the subject a pharmaceutical composition comprising apilimod, or a pharmaceutically acceptable salt thereof, optionally apilimod dimesylate, in combination with a glutamatergic agent, optionally selected from agmatine, amantadine, AP5 (R-2-amino-5-phosphonopentanoate), eliprodil, and selfotel.

In embodiments, the disclosure provides a method of treating a neurological syndrome or anxiety-related disorder in a subject in need thereof, the method comprising administering to the subject a pharmaceutical composition comprising apilimod, or a pharmaceutically acceptable salt thereof, optionally apilimod dimesylate, in combination with a glutamatergic agent, optionally selected from AP7 (2-amino-7-phosphonoheptanoic acid) and agmatine.

In embodiments, the disclosure provides a method of treating epilepsy or neuropathic pain in a subject in need thereof, the method comprising administering to the subject a pharmaceutical composition comprising apilimod, or a pharmaceutically acceptable salt thereof, optionally apilimod dimesylate, in combination with a glutamatergic agent, optionally selected from CPPene (3-[(R)-2-carboxypiperazin-4-yl]-prop-2-enyl-1-phosphonic acid), NBQX (2,3-dihydroxy-6-nitro-7-sulfamoyl-benzo[f]quinoxaline-2,3-dione), and selfotel.

In embodiments, the disclosure provides a method of treating Parkinson's disease, Parkinsonism syndrome, or multiple sclerosis in a subject in need thereof, the method comprising administering to the subject a pharmaceutical composition comprising apilimod, or a pharmaceutically acceptable salt thereof, optionally apilimod dimesylate, in combination with a glutamatergic agent, optionally amantadine.

In embodiments, the disclosure provides a method of treating attention deficit hyperactivity disorder (ADHD) in a subject in need thereof, the method comprising administering to the subject a pharmaceutical composition comprising apilimod, or a pharmaceutically acceptable salt thereof, optionally apilimod dimesylate, in combination with a glutamatergic agent, optionally atomoxetine.

In embodiments, the disclosure provides a method of treating depression in a subject in need thereof, the method comprising administering to the subject a pharmaceutical composition comprising apilimod, or a pharmaceutically acceptable salt thereof, optionally apilimod dimesylate, in combination with a glutamatergic agent, optionally selected from agmatine, delucemin, and lanicemine.

In embodiments, the disclosure provides a method of treating cancer in a subject in need thereof, the methods comprising administering to the subject a pharmaceutical composition comprising apilimod, or a pharmaceutically acceptable salt thereof, optionally apilimod dimesylate, in combination with a glutamatergic agent. In embodiments, the cancer expresses the metabotropic glutamate receptor 1 (GRM1). In embodiments, the cancer is an inoperable or metastatic advanced solid tumor or a lymphoma. In embodiments, the cancer is selected from brain cancer (including glioma and glioblastoma), breast cancer, cervical cancer, colorectal cancer, leukemia, lung cancer, lymphoma, melanoma or other skin cancer, ovarian cancer, prostate cancer, renal cancer, and testicular cancer. In embodiments, the cancer is melanoma or breast cancer. In embodiments, the glutamatergic agent is selected from a glutamate transporter modulating agent and a glutamate receptor antagonist. In embodiments, the glutamate transporter modulating agent is an excitatory amino acid reuptake inhibitor. In embodiments, the glutamate receptor antagonist is an N-methyl-D-aspartate (NMDA) receptor antagonist. In embodiments, the glutamate receptor antagonist is selected from AP5 (R-2-amino-5-phosphonopentanoate), AP7 (2-amino-7-phosphonoheptanoic acid), CNQX (6-cyano-7-nitroquinoxaline-2,3-dione), CPPene (3-[(R)-2-carboxypiperazin-4-yl]-prop-2-enyl-1-phosphonic acid), NBQX (2,3-dihydroxy-6-nitro-7-sulfamoyl-benzo[f]quinoxaline-2,3-dione), and selfotel (CGS-19755). In embodiments, the glutamate receptor antagonist is selected from amantadine, atomoxetine, AZD6765, agmatine, gacyclidine, ketamine, memantine, eliprodil, delucemin. In embodiments, the glutamatergic agent is selected from BHV-5000, lamotrigine, lanicemine, riluzole, trigriluzole, and topiramate. In embodiments, the glutamatergic agent is trigriluzole.

A "subject in need thereof" refers to a subject in need of treatment for a neurological disease or disorder, or a cancer. In embodiments, the subject in need is one that is "non-responsive" or "refractory" to a standard therapy for the neurological disease or disorder, or the cancer. In this context, the terms "non-responsive" and "refractory" refer to the subject's response to therapy as not clinically adequate to relieve one or more symptoms associated with the neurological disease or disorder, or the cancer. In embodiments, the patient in need of treatment of is one having repeat expansions in the C9ORF72 gene, for example, in embodiments relating to a neurological disease or disorder, especially ALS or frontotemporal dementia.

A "subject" refers generally to a mammal. The mammal can be e.g., a human, primate, mouse, rat, dog, cat, cow, horse, goat, camel, sheep or a pig. Preferably, the subject is a human. The terms "subject" and "patient" are used interchangeably herein.

The terms, "treatment", "treating" or "treat" describes the management and care of a subject having a neurological disease or disorder, or a cancer, as described here and includes the administration of a therapeutic agent, or combination thereof as described here, to slow the progression of the disease or disorder and/or to alleviate one or more symptoms of the neurological disease or disorder, or the cancer. In this context, treating includes administering an amount of the therapeutic agent, or combination of agents, effective to alleviate one or more symptoms of the neurological disease or disorder, or the cancer. The term "alleviate" refers to a process by which the severity of a symptom is reduced or decreased, but it may not necessarily be eliminated, although it may be eliminated for a period of time, or temporarily. While elimination of the symptom is preferred, it is not required. The terms, "prevention", "preventing" or "prevent" refer to reducing or eliminating the onset of a symptom, especially in the context of preventing the progression of the disease or disorder, or the cancer, where progression is defined by the onset one or more symptoms.

The term "therapeutically effective amount" refers to an amount sufficient to treat, ameliorate a symptom of, reduce the severity of, or reduce the duration of the neurological disease or disorder, or the cancer, or to enhance or improve the therapeutic effect of another therapy. The precise effective amount for a subject will depend upon the subject's body weight, size, and health; the nature and extent of the condition; and the therapeutic or combination of therapeutics selected for administration.

An effective amount of apilimod can be administered once daily, from two to five times daily, up to two times or up to three times daily, or up to eight times daily. In embodiments, the apilimod is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

An effective amount of apilimod, or a pharmaceutically acceptable salt, solvate, clathrate, hydrate, polymorph, metabolite, prodrug, analog or derivative thereof, can range from about 0.001 mg/kg to about 1000 mg/kg, more preferably 0.01 mg/kg to about 100 mg/kg, more preferably 0.1 mg/kg to about 10 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents. See, e.g., U.S. Pat. No. 7,863,270, incorporated herein by reference.

In more specific aspects, apilimod or a pharmaceutically acceptable salt, solvate, clathrate, hydrate, polymorph, metabolite, prodrug, analog or derivative thereof, is administered at a dosage regimen of 30-300 mg/day (e.g., 30, 35, 40, 45, 50, 55, 60, 65, 70, 75, 80, 85, 90, 95, 100, 125, 150, 175, 200, 225, 250, 275, or 300 mg/day) for at least 1 week (e.g., 1, 2, 3, 4, 5, 6, 7, 8, 9, 10, 11, 12, 36, 48, or more weeks). Preferably, a compound of the disclosure is administered at a dosage regimen of 100-300 mg/day for 4 or 16 weeks. Alternatively or subsequently, a compound of the disclosure is administered at a dosage regimen of 100 mg twice a day for 8 weeks, or optionally, for 52 weeks.

Pharmaceutical Compositions and Formulations

The disclosure provides pharmaceutical compositions comprising apilimod, or a pharmaceutically acceptable salt, solvate, clathrate, hydrate, polymorph, metabolite, prodrug, analog or derivative thereof, for use in combination therapy with a glutamatergic agent in the treatment of a neurological disease or disorder, or in the treatment of cancer.

The disclosure also provides pharmaceutical compositions comprising an amount of apilimod, or a pharmaceutically acceptable salt, solvate, clathrate, hydrate, polymorph, metabolite, prodrug, analog or derivative thereof, in combination with a glutamatergic agent and, optionally, at least one pharmaceutically acceptable excipient or carrier, wherein the amount is effective for the treatment of a neurological disease or disorder, or a cancer.

In embodiments, the apilimod, or a pharmaceutically acceptable salt, solvate, clathrate, hydrate, polymorph, metabolite, prodrug, analog or derivative thereof, is combined with a glutamatergic agent in a single dosage form. In embodiments, the pharmaceutical composition further comprises an antioxidant.

A "pharmaceutical composition" is a formulation containing one or more therapeutic agents in a pharmaceutically acceptable form suitable for administration to a subject. The term "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in $m^2$, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

For example, the dosage unit form can comprise 1 nanogram to 2 milligrams, or 0.1 milligrams to 2 grams; or from 10 milligrams to 1 gram, or from 50 milligrams to 500 milligrams or from 1 microgram to 20 milligrams; or from 1 microgram to 10 milligrams; or from 0.1 milligrams to 2 milligrams.

The pharmaceutical compositions can take any suitable form (e.g, liquids, aerosols, solutions, inhalants, mists, sprays; or solids, powders, ointments, pastes, creams, lotions, gels, patches and the like) for administration by any desired route (e.g, pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the disclosure may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present disclosure with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present disclosure may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present disclosure together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present disclosure may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present disclosure as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present disclosure can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the disclosure are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present disclosure also provides packaging and kits comprising pharmaceutical compositions for use in the methods of the present disclosure. The kit can comprise one or more containers selected from the group consisting of a bottle, a vial, an ampoule, a blister pack, and a syringe. The kit can further include one or more of instructions for use in treating and/or preventing a disease, condition or disorder of the present disclosure, one or more syringes, one or more applicators, or a sterile solution suitable for reconstituting a pharmaceutical composition of the present disclosure.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

Example 1

In patients treated with apilimod there are alterations in various proteins circulating in the blood plasma. One of these is Glycoprotein Nonmetastatic Melanoma Protein B (GPNMB), a type I membrane protein originally identified in melanoma cells. In addition to expression on the cell surface, it can also be released (or shed) from cells by the activity of matrix metalloproteases such as ADAM10 and ADAM12.

Expression of GPNMB increases significantly in the spinal cords of patients with ALS and this is accompanied by an increase in shed GPNMB in sera. A mouse model, which is based on the known mutation of Superoxide Dismutase 1 (SOD1$^{G93A}$) found in familial cases of ALS replicates, many of the features of the human disease including the increase in GPNMB. In this model, further increasing the levels of GPNMB prolongs survival, delays onset, and protects skeletal muscle from denervation and atrophy. The effects of GPNMB are likely mediated through the extracellular, shed form of GPNMB, since the latter can directly attenuate SOD1$^{G93A}$ induced neural cell death in culture, as reported previously in Nagahara et al. (2016) *J. Neuroscience*. Neuroprotective effects have also been demonstrated in a mutant transactive response DNA binding protein 43 kDa (TDP-43) cell culture model suggesting protection across ALS predisposing mutations.

Accordingly, we investigated whether apilimod treatment in humans increased the levels of shed GPNMB.

A SOMAscan™ platform was used to identify analytes that were changed in the plasma of patients upon apilimod dosing. SOMAscan™ is an aptamer-based proteomics assay from SomaLogic capable of measuring 1,305 human protein analytes in serum or plasma with high sensitivity and specificity. Plasma from patients enrolled in the clinical trial designated NCT02594384 was collected pre-dose (before the first administration of apilimod) and after 14 days of dosing with apilimod, on day 15. Using differential protein analysis with a paired experimental design for linear models of microarray data using the "Limma R" software package described by Ritchie et al. in Nucleic Acids Research, 43(7), pp. e47 (2015).

GPNMB was identified as the analyte that showed the highest average fold change (4-fold) among the analytes that were significantly changed (FDR<0.05) (FIG. 1). Thus, apilimod dosing consistently increased the plasma levels of GPNMB in treated patients. These results indicate that apilimod treatment may ameliorate the neuromuscular degradation found in ALS, and potentially improve patient survival. In addition, since riluzole is the current standard of care treatment for ALS, we anticipate that combination therapy with apilimod and riluzole will provide significant improvements in the treatment of ALS compared to either apilimod or riluzole therapy alone.

What is claimed is:

1. A method for treating a neurological disease or disorder in a subject in need thereof, the method comprising administering to the subject a pharmaceutical composition comprising apilimod, or a pharmaceutically acceptable salt thereof, in combination with a glutamatergic agent.

2. The method of claim 1, wherein the apilimod is apilimod dimesylate.

3. The method of claim 1, wherein the glutamatergic agent is selected from a glutamate transporter modulating agent and a glutamate receptor antagonist.

4. The method of claim 3, wherein the glutamate transporter modulating agent is an excitatory amino acid reuptake inhibitor.

5. The method of claim 3, wherein the glutamate receptor antagonist is an N-methyl-D-aspartate (NMDA) receptor antagonist.

6. The method of claim 3, wherein the glutamate receptor antagonist is selected from AP5 (R-2-amino-5-phosphonopentanoate), AP7 (2-amino-7-phosphonoheptanoic acid), CNQX (6-cyano-7-nitroquinoxaline-2,3-dione), CPPene (3-[(R)-2-carboxypiperazin-4-yl]-prop-2-enyl-1-phosphonic acid), NBQX (2,3-dihydroxy-6-nitro-7-sulfamoyl-benzo[f]quinoxaline-2,3-dione), and selfotel (CGS-19755).

7. The method of claim 3, wherein the glutamate receptor antagonist is selected from amantadine, atomoxetine, AZD6765, agmatine, gacyclidine, ketamine, memantine, eliprodil, delucemin.

8. The method of claim 1, wherein the glutamatergic agent is selected from BHV-5000, lamotrigine, lanicemine, riluzole, trigriluzole, and topiramate.

9. The method of claim 1, wherein the pharmaceutical composition is an oral dosage form or a sublingual dosage form.

10. The method of claim 1, wherein the glutamatergic agent is administered in the same or a different dosage form as the apilimod.

11. The method of claim 1, wherein the neurological disease or disorder is selected from Alzheimer's disease, amyotrophic lateral sclerosis (ALS), attention deficit hyperactivity disorder, autism, cerebellar ataxia, Charcot-Marie-Tooth disease, Creutzfeldt-Jakob disease, dementia, epilepsy, Friedreich's ataxia, Huntington's disease, multiple sclerosis, obsessive compulsive disorder (OCD), Parkinson's disease, Rett syndrome, senile chorea, spinal ataxia, spinal cord injury, supranuclear palsy, traumatic brain injury.

12. The method of claim 11, wherein the neurological disease or disorder is dementia.

13. The method of claim 12, wherein the dementia is selected from AIDS dementia complex (ADC), dementia associated with Alzheimer's disease (AD), dementia pugilistica, diffuse Lewy body disease, frontotemporal dementia, mixed dementia, senile dementia of Lewy body type, and vascular dementia.

14. The method of claim 11, wherein the neurological disease or disorder is amyotrophic lateral sclerosis (ALS).

15. The method of claim 11, wherein the neurological disease or disorder is Rett syndrome.

16. The method of claim 11, wherein the neurological disease or disorder is obsessive compulsive disorder (OCD).

17. The method of claim 1, wherein the subject is human.

18. A method for treating amyotrophic lateral sclerosis (ALS) in a subject in need thereof, the method comprising administering to the subject a pharmaceutical composition comprising apilimod, or a pharmaceutically acceptable salt thereof, in combination with a glutamatergic agent selected from riluzole and trigriluzole.

19. A method for treating Alzheimer's disease in a subject in need thereof, the method comprising administering to the subject a pharmaceutical composition comprising apilimod, or a pharmaceutically acceptable salt thereof, in combination with a glutamatergic agent selected from riluzole and trigriluzole.

20. A method for treating obsessive compulsive disorder (OCD) in a subject in need thereof, the method comprising administering to the subject a pharmaceutical composition comprising apilimod, or a pharmaceutically acceptable salt thereof, in combination with a glutamatergic agent selected from riluzole and trigriluzole.

21. A method for treating Rett syndrome in a subject in need thereof, the method comprising administering to the subject a pharmaceutical composition comprising apilimod, or a pharmaceutically acceptable salt thereof, in combination with a glutamatergic agent selected from BHV-5000, and lanicemine.

22. A method of treating cancer in a subject in need thereof, the methods comprising administering to the subject a pharmaceutical composition comprising apilimod, or a pharmaceutically acceptable salt thereof, in combination with a glutamatergic agent selected from riluzole and trigriluzole, wherein the cancer is selected from brain cancer, breast cancer, cervical cancer, colorectal cancer, leukemia, lung cancer, lymphoma, melanoma or other skin cancer, ovarian cancer, prostate cancer, renal cancer, and testicular cancer.

23. A pharmaceutical composition comprising apilimod and a glutamatergic agent, and a pharmaceutically carrier.

24. The pharmaceutical composition of claim 23, wherein the apilimod is apilimod dimesylate.

25. The pharmaceutical composition of claim 23, wherein the glutamatergic agent is selected from a glutamate transporter modulating agent and a glutamate receptor antagonist.

26. The pharmaceutical composition of claim 25, wherein the glutamate transporter modulating agent is an excitatory amino acid reuptake inhibitor.

27. The pharmaceutical composition of claim 25, wherein the glutamate receptor antagonist is an N-methyl-D-aspartate (NMDA) receptor antagonist.

28. The pharmaceutical composition of claim 25, wherein the glutamate receptor antagonist is selected from amantadine, atomoxetine, AZD6765, agmatine, gacyclidine, memantine, eliprodil, delucemin.

29. The pharmaceutical composition of claim 23, wherein the glutamatergic agent is selected from riluzole, trigriluzole, BHV-5000, and lanicemine.

30. The method of claim 22, wherein the glutamatergic agent is trigriluzole.

* * * * *